United States Patent
Benson

(10) Patent No.: US 9,446,252 B2
(45) Date of Patent: Sep. 20, 2016

(54) SYSTEM AND METHOD FOR RESETTING AN IMPLANTABLE MEDICAL DEVICE

(75) Inventor: Dennis Benson, McKinney, TX (US)

(73) Assignee: ADVANCED NEUROMODULATION SYSTEMS, INC., Plano, TX (US)

(*) Notice: Subject to any disclaimer, the term of this patent is extended or adjusted under 35 U.S.C. 154(b) by 1004 days.

(21) Appl. No.: 13/593,233

(22) Filed: Aug. 23, 2012

(65) Prior Publication Data

US 2013/0096648 A1    Apr. 18, 2013

Related U.S. Application Data

(60) Provisional application No. 61/548,614, filed on Oct. 18, 2011.

(51) Int. Cl.
*A61N 1/372* (2006.01)
*A61N 1/05* (2006.01)
*A61N 1/36* (2006.01)

(52) U.S. Cl.
CPC ......... *A61N 1/37252* (2013.01); *A61N 1/0551* (2013.01); *A61N 1/36071* (2013.01)

(58) Field of Classification Search
CPC .................. A61N 1/37252; A61N 1/37223
USPC ......................................................... 607/60
See application file for complete search history.

(56) References Cited

U.S. PATENT DOCUMENTS

| | | | | |
|---|---|---|---|---|
| 4,124,031 A | * | 11/1978 | Mensink | A61N 1/37217 607/31 |
| 6,963,779 B1 | * | 11/2005 | Shankar | A61N 1/37217 607/30 |
| 2009/0058636 A1 | * | 3/2009 | Gaskill | A61N 1/37282 340/539.11 |

* cited by examiner

*Primary Examiner* — Christopher D Koharski
*Assistant Examiner* — Roland Dinga

(57) ABSTRACT

In one embodiment, a method, of operating an implantable medical device, comprises: (i) operating reset logic within the implantable medical device that is independently operable from a processor of the implantable medical device after the implantable medical device is implanted within a patient, wherein the processor is adapted for central control of the implantable medical device; (ii) operating a magnetic field sensor in the implantable medical device; (iii) generating digital data using, at least, the magnetic field sensor; (iv) detecting, by the reset logic, a digital key in the digital data; (v) in response to (iv), asserting a reset signal on a pin of the processor by the reset logic; and (vi) conducting reset operations in the processor in response to the reset signal.

6 Claims, 3 Drawing Sheets

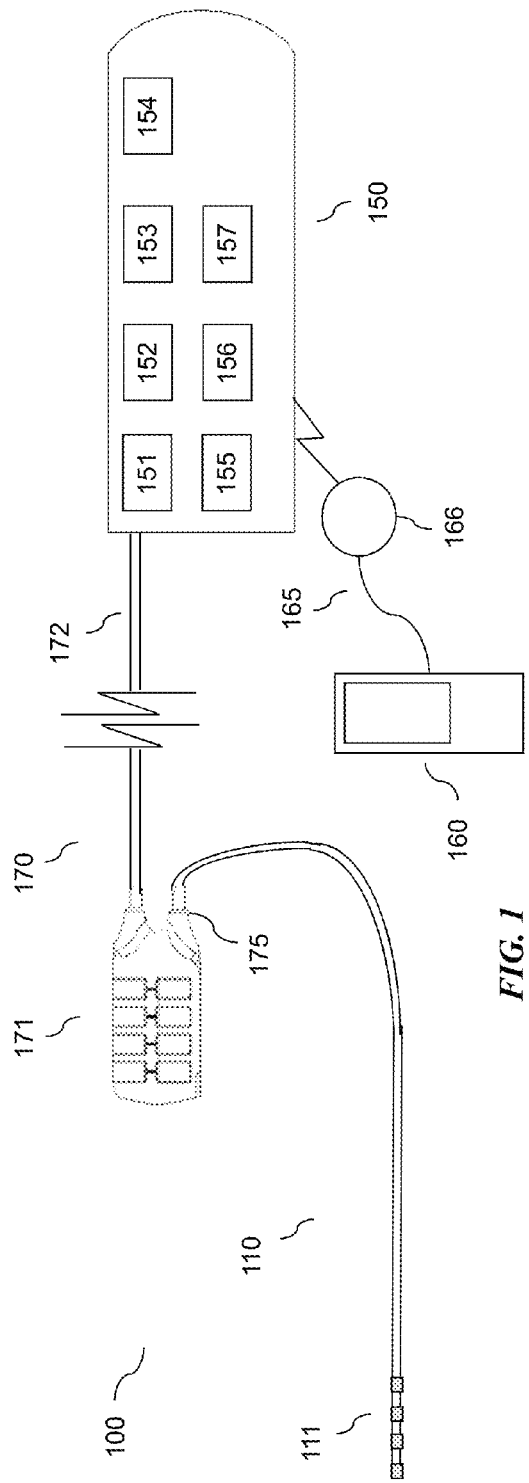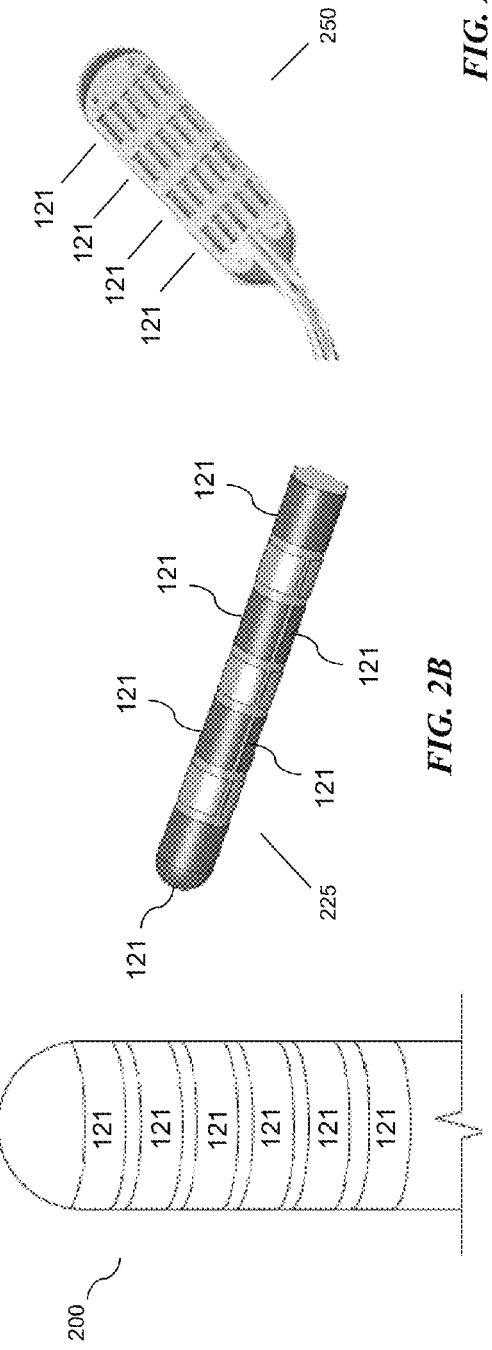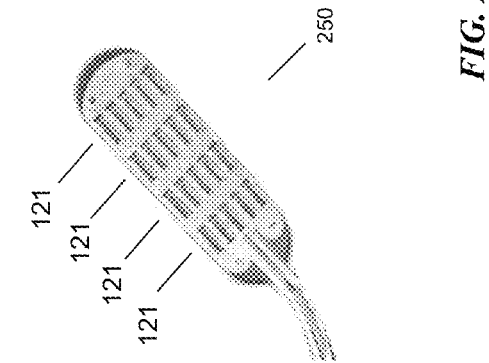

SYSTEM AND METHOD FOR RESETTING AN IMPLANTABLE MEDICAL DEVICE

TECHNICAL FIELD

This application is generally related to implantable medical devices (e.g., implantable pulse generators) that are resettable and methods of resetting implantable medical devices.

BACKGROUND

The medical device industry produces a wide variety of electronic and mechanical devices for addressing patient medical conditions. Clinicians use medical devices alone or in combination with drug therapies and surgery to address numerous patient medical conditions. Medical devices may provide the best and sometimes the only therapy for selected medical conditions and disorders. Common implantable medical devices include neurostimulation systems, pacemakers, defibrillators, drug delivery pumps, and diagnostic recorders.

For example, neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

SUMMARY

In one embodiment, a method, of operating an implantable medical device, comprises: (i) operating reset logic within the implantable medical device that is independently operable from a processor of the implantable medical device after the implantable medical device is implanted within a patient, wherein the processor is adapted for central control of the implantable medical device; (ii) operating a magnetic field sensor in the implantable medical device; (iii) generating digital data using, at least, the magnetic field sensor; (iv) detecting, by the reset logic, a digital key in the digital data; (v) in response to (iv), asserting a reset signal on a pin of the processor by the reset logic; and (vi) conducting reset operations in the processor in response to the reset signal.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1 depicts a stimulation system according to some representative embodiments.

FIG. 2A depicts one electrode configuration at the distal end of a lead that may be employed in stimulator systems according to some representative embodiments.

FIG. 2B depicts another electrode configuration at the distal end of a lead that may be employed in stimulator systems according to some representative embodiments.

FIG. 2C depicts another electrode configuration at the distal end of a lead that may be employed in stimulator systems according to some representative embodiments.

DETAILED DESCRIPTION

Figure 3:
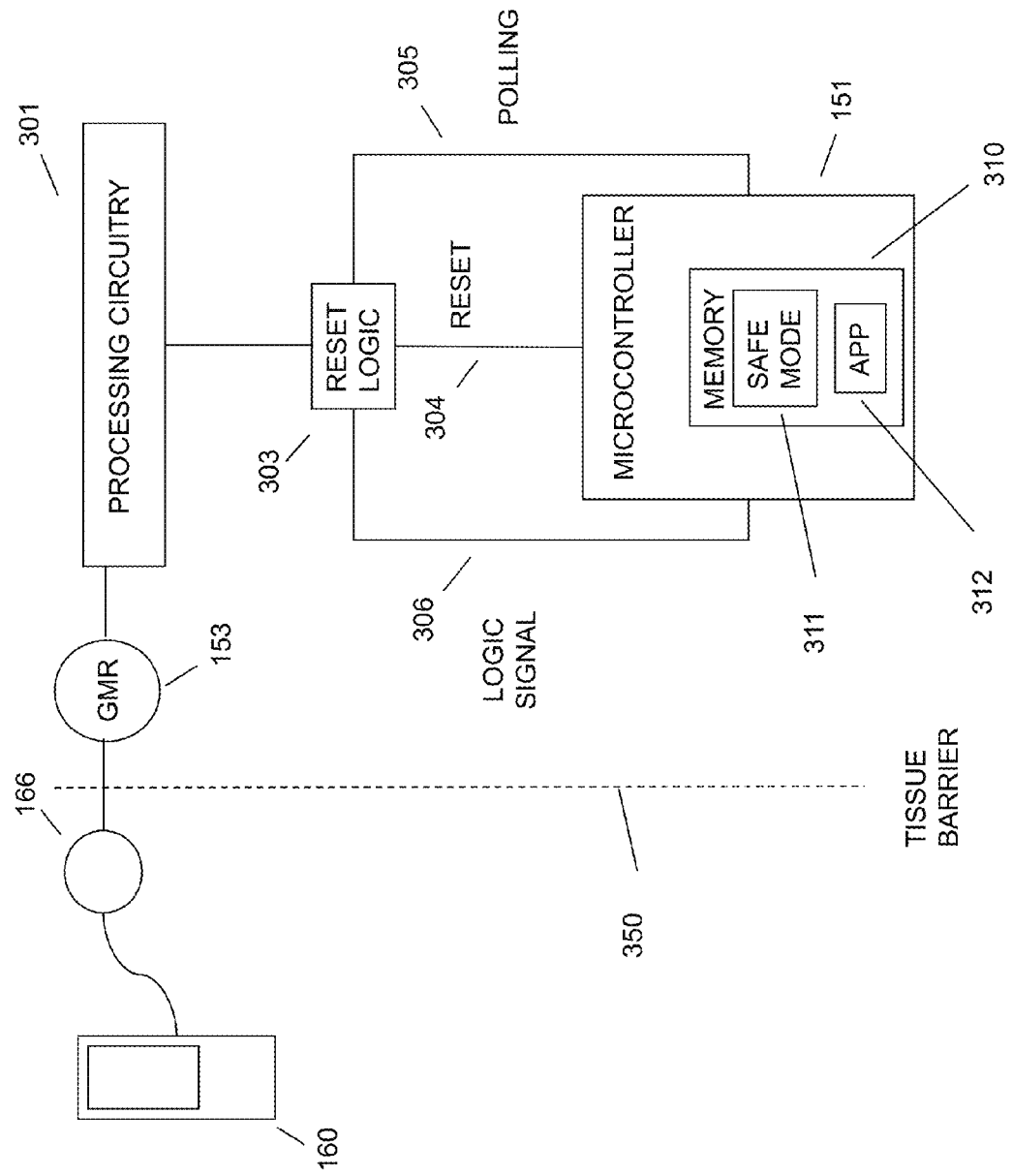
FIG. 3 depicts circuitry involved in a reset operation of an implanted medical device according to some representative embodiments.

FIG. 1 depicts stimulation system 100 that generates electrical pulses for application to tissue of a patient according to some representative embodiments. For example, system 100 may be adapted to stimulate spinal cord tissue, peripheral nerve tissue, deep brain tissue, cortical tissue, cardiac tissue, digestive tissue, pelvic floor tissue, or any other suitable tissue within a patient's body. Although a stimulation system is described according to some embodiments, any implantable medical device may be reset according to other embodiments.

The stimulation system includes implantable pulse generator 150 that is adapted to generate electrical pulses for application to tissue of a patient. Implantable pulse generator 150 typically comprises a metallic housing that encloses controller 151, pulse generating circuitry 152, charging component 153, battery 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the pulse generator 150 for execution by the microcontroller or processor to control the various components of the device.

Although not required, in this specific embodiment, pulse generator 150 comprises attached extension component 170. That is, in lieu of providing a separate extension lead that is physically placed within a header of an IPG by the surgeon during implant, extension component 170 is directly attached to and is non-removable from pulse generator 150 according to some representative embodiments. Other embodiments may employ a separate extension component 170 for connecting stimulation lead 110 with the generator 150. Alternatively, stimulation lead 110 may be directly coupled within the header of the generator 150. Within pulse generator 150, electrical pulses are generated by pulse generating circuitry 152 and are provided to switching circuitry 157. The switching circuit connects to output wires, traces, lines, or the like (not shown in FIG. 1) which are, in turn, electrically coupled to internal conductive wires (not shown in FIG. 1) of lead body 172 of extension component 170. The conductive wires, in turn, are electrically coupled to electrical connectors (e.g., "Bal-Seal" connectors) within connector portion 171 of extension component 170.

The terminals of one or more stimulation leads 110 are inserted within port 175 of connector portion 171 for electrical connection with respective electrical connectors (not shown) within connector portion 171. Connector portion 171 may include one or more set-screw mechanisms (not shown) to secure the lead(s) 110 within connector portion 171. The pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171. Also, connector portion 171 may include multiple ports 175 for receipt of a suitable number of stimulation leads 110.

Although not required, extension component 170 is arranged to place port 175 in a specific arrangement relative to the housing of pulse generator 150 (as shown in FIG. 1). Specifically, when lead body 172 is disposed in a linear configuration and extends away substantially perpendicularly from the housing of pulse generator 150, port 175 preferably faces the housing of pulse generator 150. That is, at least one port 175 is on the side of extension component 170 that is proximal to housing of pulse generator 150, i.e. the side on which lead body 172 meets connector portion 171. Also, when the terminals of lead 110 are placed within connector portion 171, lead 110 initially extends back toward the housing of pulse generator 150. In other embodiments, any suitable form factor may be employed for generator 150 according to other embodiments. Also, extension component 170 may be implemented as a separate discrete component from generator 150 as is known in the art.

Also, at any suitable time, the clinician may input data into controller device 160 (see below) indicating the ports 175 in which leads 110 are placed, thereby permitting controller device 160 to properly correlate the various electrodes and terminals of lead 110 to the corresponding electrical connectors of connector portion 171.

For implementation of the components within pulse generator 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors. Likewise, connector portion 171 may comprise any suitable number of electrical connectors and lead body 172 may comprise any suitable number of conductors.

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Provisional Patent Application Ser. No. 61/247,360, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure. Any suitable stimulation portion design may be employed for lead 110.

Although not required for all embodiments, the lead bodies of lead(s) 110 and extension component 170 may be fabricated to flex and elongate in response to patient movements upon implantation within the patient. By fabricating lead bodies according to some embodiments manner, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

Controller device 160 may be implemented to recharge battery 154 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 154 by charging circuitry 156. Charging circuitry 156 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

As previously discussed, implantable pulse generators (and typically many active implantable medical devices) include a processor, microcontroller, or similar circuitry to control the operations of the device. The electronics of such devices are subject to faults. Many of the faults are mitigated by known fault handling mechanisms implemented within software of the device. However, there are number of faults that are not subject to mitigation through conventional fault handling mechanisms. For example, if a critical bit in flash memory becomes flipped, the implanted device may become inoperable or may operate in an unintended, unacceptable manner. The communication capabilities of the device may also be lost thereby making device diagnostics impossible.

In such conventional circumstances, the implanted device is simply explanted from the patient and replaced with another device.

Some representative embodiments provide a mechanism for resetting an implantable medical device into a safe mode or a boot mode (using a modulated magnetic). From the safe mode or boot mode, it may be possible to diagnose device faults and repair the faults (if necessary). For example, from the safe mode or boot mode, any memory corruption of the device may be corrected by rewriting the device code through wireless communications supported by the safe mode or boot mode. As used herein, the term "reset" is intended to take its ordinary meaning as applied to a reset of a processor. As known in the art, a reset typically involves placing related logic elements or peripherals (that are controlled by the processor) into a known state. Also, the reset typically involves "vectoring" to a known location to begin execution of binary code at that location, where the binary code invokes certain initialization operations.

FIG. 3 depicts controller 160 and a portion of pulse generator 150 during reset operations according to one representative embodiment. Controller 160 may include suitable code for initiating a reset operation when pulse generator 150 becomes non-functional. The reset operation may be employed to attempt to diagnose any potential issues and to reestablish operation of pulse generator 150 (if possible). By attempting such operations, some amount of otherwise unnecessary explant surgeries may be avoided.

In operation, controller 160 may drive current through coil 166 to generate a modulated magnetic field. In some embodiments, controller 160 initially drives a RF signal through coil 166. When coil 166 is placed adjacent to magnetic receiver component 153 of pulse generator 150 (across the tissue barrier 350), the magnetic field causes component 153 to generate a signal related to the modulated magnetic field. The generated signal is then optionally processed by circuitry 301 (if deemed necessary).

In one embodiment, component 153 may be implemented using a giant magnetoresistive (GMR) device or sensor. GMR sensors typically employ thin film structures composed of ferromagnetic alloys sandwiched around an ultra-thin nonmagnetic conducting middle layer. The thin film structures exhibit a large change in resistance (typically 10 to 20%) when the sensors are subjected to a magnetic field, compared with a maximum sensitivity of a few percent for other types of magnetic sensors. That is, ferromagnetic layers transition between anti-parallel and parallel magnetic moments depending upon whether an external magnetic field is applied. In turn, the anti-parallel and parallel orientations of the ferromagnetic layers changes the resistance of the conductive layer via electron spin states in the ferromagnetic layers adjacent to the conductive layer. Digital GMR sensors are commercially available (such as from NVE Corporation, Eden Prairie, Minn.) which may be employed for component 153.

Circuitry 301 may be optionally employed to process (e.g., filter, demodulate, etc.) the time-varying signal from component 153 and communicates a bit stream generated by the processing operations to reset logic 303. Reset logic 303 stores a window of the bit stream in memory reset logic 303. Reset logic 303 monitors the bit stream to identify one or more predefined sequence of bits. The predefined sequence of bits may define a key to cause reset logic 303 to reset controller 151 or to cause controller 151 to execute code 311 that defines a safe mode of operations of pulse generator 150. Reset logic 303 may be implemented using any suitable electronic logic circuitry according to, for example, conventional digital logic design techniques. If desired, a limited set of instructions may be stored in electronic memory for implementation of reset logic 303.

In some embodiments, reset logic 303 is connected to the reset pin of controller 151 through reset line 304. In the event that reset logic 303 detects the appropriate reset key in the bit stream generated from the modulated magnetic field, reset logic 303 asserts a suitable logic signal on line 304. The signal on line 304 causes controller 151 to conduct a reset (which is known in the art). That is, controller 151 begins to execute code programmed into its non-volatile memory 310 such as a bootstrap loader program. The bootstrap loader program may initiate certain system operations and, in turn, load the fully functional application code 312 to control pulse generator 150. After communicating the defined key for a system reset, external controller 160 may then attempt to conduct conventional communications (e.g., through near field or far field telemetry) with pulse generator 150 to determine whether the pulse generator 150 has returned to a properly functioning state. If no response is obtained through telemetry attempts after communicating the reset key, it may be assumed that the reset attempt was unsuccessful in resolving the system fault.

In one embodiment, the bootstrap loader program (executed after reset) may perform a verification of or an integrity check of software or firmware code stored in memory 310 (e.g., using a checksum operation or CRC operations, etc.). If a memory error is detected, the bootstrap loader program may automatically default to a safe mode of operation (e.g., as defined by code 311).

In some embodiments, reset logic 303 may communicate other logic signals to controller 151 in an attempt to resolve a fault in pulse generator 150. As shown in the specific embodiment of FIG. 3, reset logic 303 includes polling line 305 and logic signal line 306. Rest logic 303 may set a flag via polling line 305 after a reset operation of controller 151 has occurred. When controller 151 detects the flag as set via logic signal line 306, controller 151 may then execute code stored in memory 310 of controller 151. The executed code may be adapted to permit recovery and/or repair of pulse generator 150 (e.g., to permit a re-write of system code in memory 310 or elsewhere in pulse generator 150). For example, code 311 may be adapted to implement a "safe mode" mode of operation of pulse generator 150 in which a minimum number of system operations are performed to permit software to be reloaded into pulse generator 150. The software/firmware update may be performed by code 311 using conventional operations which are known in the art.

In some embodiments, reset logic 303 may communicate different logic states on logic signal line 306. For example, reset logic 303 may communicate a vector to identify code for execution (e.g., safe mode code 311) after polling operations. Also, depending upon the data communicated in this manner, the executed code may perform different functions. For example, different data values may be employed for diagnostic operations, external communications with controller 160, software reload operations, etc.

Although it is not a critical requirement of the invention, reset logic 303 is preferably provided within pulse generator 150 to operate independently of microcontroller 151. By providing independent operation, if microcontroller 151 enters a non-recoverable state due to a hardware or software fault, it is possible to reestablish proper operation of the implant device without physically accessing the device. Further, in some embodiments, the reset operations are implemented in such a manner that extraneous signals will not inadvertently cause a device reset. A specific sequence of operations (e.g., communication of one or more digital keys) may be required as a condition before the reset signal is provided to the microcontroller or processor.

Figure 4:
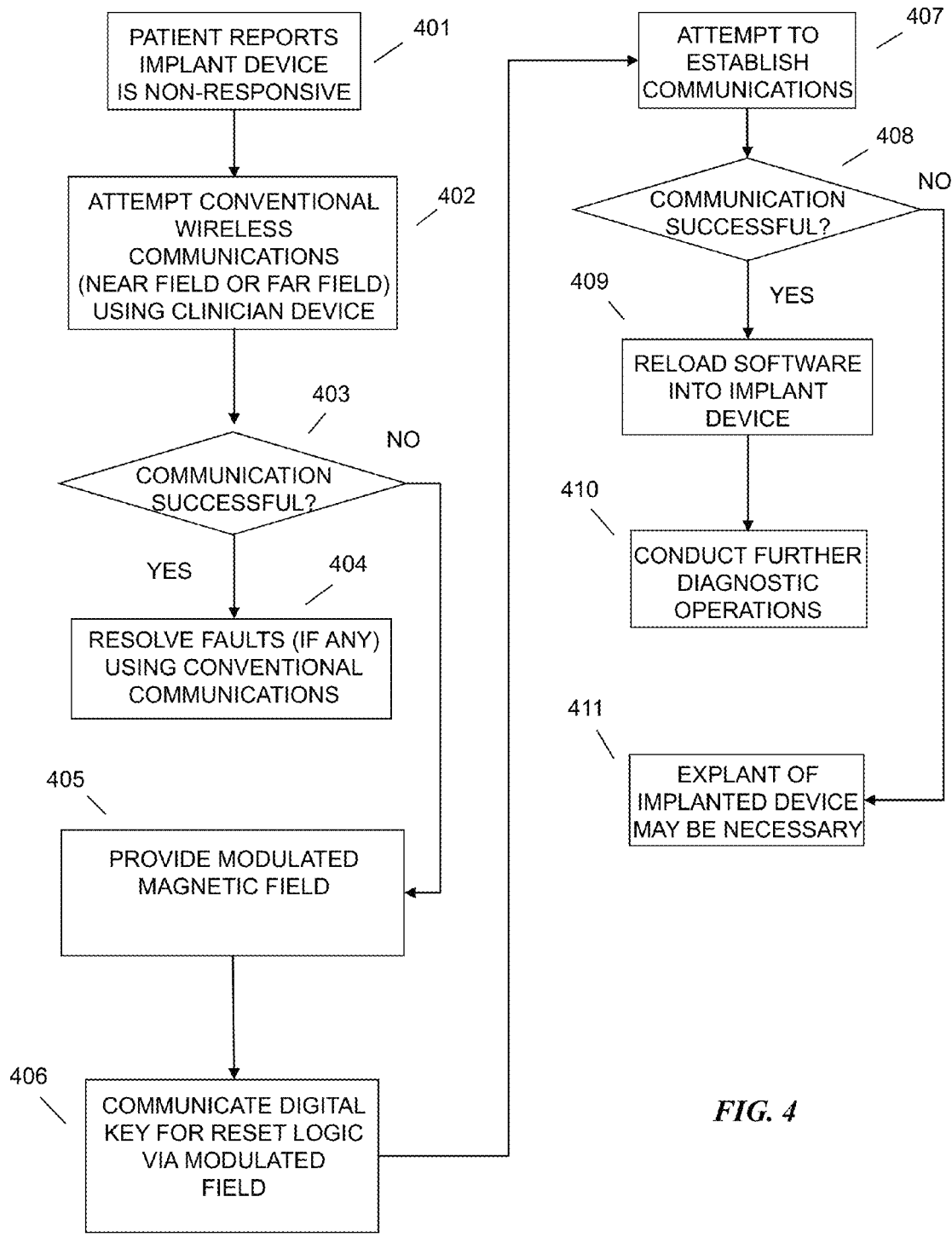
FIG. 4 depicts a flowchart of operations involved in resetting an implanted medical device according to some representative embodiments.

FIG. 4 depicts a flowchart for attempting to recover proper functioning of a medical device implanted within a patient. In 401, the patient initially reports that the patient's implant device is non-responsive. The patient may have previously noticed that the therapy provided by the implant device is no longer being delivered. Additionally or alternatively, the patient may have previously noticed that the implant device is not responsive to communication attempts by the patient's external controller device.

In 402, conventional wireless communications (near field or far field) are attempted using clinician device. In 403, it is determined whether the communication attempt was successful. If so, implant device faults (if any) are resolved using conventional communications (404).

In 405, if the conventional wireless communications are unsuccessful, a modulated magnetic field is provided. The reset functionality may require the modulated magnetic field to be provided at or near a defined frequency to permit the reset functionality to be activated (e.g., using band-pass filtering of the resulting signal in the pulse generator).

In 406, a digital key is communicated for the reset logic of the pulse generator via the modulated magnetic field. Although a digital key is mentioned according to some embodiments, any suitable message sequence, format, or protocol may be employed according to other embodiments. Upon receipt, the reset logic of the device (assuming some level of operability still exists in the implanted device) causes the microcontroller or processor to be reset by asserting a suitable logic signal on the reset pin of the microcontroller or processor. A safe mode of operation may be employed upon reset. The safe mode may be initiated using further operations of the reset logic (e.g., according to a parameter value communicated with or after the reset key). Alternatively, the safe mode of operation may be a default state after reset.

After attempting reset operations by communication of the digital key, in 407, an attempt to establish communications with the implanted medical device is performed (e.g., using near field or far field communications). In 408, it is determined whether the communication attempt was successful. If successful, software is reloaded into implant device (409) and further diagnostic operations may be optionally performed (410), if desired. The software/firmware update may be performed using conventional protocols, which are known in the art, or any subsequently developed protocol. If the communications attempt is not successful, it is concluded that an explant procedure to remove the implanted device from the patient's body may be necessary (411).

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of operating an implantable medical device, comprising
   (i) operating reset logic within the implantable medical device that is independently operable from a processor of the implantable medical device after the implantable medical device is implanted within a patient, wherein the processor is adapted for central control of the implantable medical device;
   (ii) operating a magnetic field sensor in the implantable medical device;
   (iii) generating digital data using, at least, the magnetic field sensor;
   (iv) detecting, by the reset logic, a digital key in the digital data;
   (v) in response to (iv), asserting a reset signal on a pin of the processor by the reset logic;
   (vi) conducting reset operations in the processor in response to the reset signal; and
   (v) after resetting the processor, causing the processor to enter a safe mode of operations, wherein the safe mode of operations is defined by a first set of software instructions that are different from a second set of software instructions of an application mode of operations wherein the application mode of operations controls provision of a therapy by the implantable medical device to the patient, wherein the safe mode includes execution of code for conducting wireless communications to perform a software or firmware update for the implantable medical device.

2. The method of claim 1 further comprising: performing an integrity check of software or firmware of the implantable medical device.

3. The method of claim 1 wherein the reset logic is connected to the processor by a polling line.

4. The method of claim 3 wherein the reset logic is operable to cause the processor to execute software instructions defining the safe mode of operation by communicating a signal on the poling line after the reset operations of (vi).

5. The method of claim 1 wherein the magnetic field sensor is a giant magnetoresistive (GMR) sensor.

6. The method of claim 5 wherein the GMR sensor is a digital sensor.

* * * * *